United States Patent
Gil et al.

(10) Patent No.: US 12,109,044 B2
(45) Date of Patent: Oct. 8, 2024

(54) BIO-SIGNAL MEASUREMENT MEANS AND BIO-SIGNAL MONITORING SYSTEM

(71) Applicant: HUINNO CO., LTD, Seoul (KR)

(72) Inventors: Yeong Joon Gil, Seoul (KR); Sung Hoon Jung, Busan (KR)

(73) Assignee: HUINNO CO., LTD, Seoul (KR)

( * ) Notice: Subject to any disclaimer, the term of this patent is extended or adjusted under 35 U.S.C. 154(b) by 1012 days.

(21) Appl. No.: 17/018,568

(22) Filed: Sep. 11, 2020

(65) Prior Publication Data

US 2021/0000419 A1    Jan. 7, 2021

Related U.S. Application Data

(63) Continuation-in-part of application No. 15/393,727, filed on Dec. 29, 2016, now abandoned, which is a
(Continued)

(30) Foreign Application Priority Data

May 20, 2015 (KR) .......................... 10-2015-0070249

(51) Int. Cl.
| | |
|---|---|
| A61B 5/00 | (2006.01) |
| A61B 5/0205 | (2006.01) |
| A61B 5/1455 | (2006.01) |
| A61B 5/318 | (2021.01) |
| A61B 5/332 | (2021.01) |
| H04R 1/10 | (2006.01) |

(Continued)

(52) U.S. Cl.
CPC ........ *A61B 5/6817* (2013.01); *A61B 5/02055* (2013.01); *A61B 5/14552* (2013.01); *A61B 5/318* (2021.01); *A61B 5/332* (2021.01); *A61B 5/6815* (2013.01); *H04R 1/1091* (2013.01); *A61B 5/01* (2013.01); *A61B 5/02416* (2013.01); *A61B 5/02438* (2013.01); *A61B 5/0245* (2013.01); *A61B 5/14551* (2013.01); *A61B 2562/06* (2013.01); *A61B 2562/227* (2013.01); *H04R 1/1016* (2013.01)

(58) Field of Classification Search
CPC ..... A61B 5/318; A61B 6/6815; A61B 5/6815; A61N 1/36036
See application file for complete search history.

(56) References Cited

U.S. PATENT DOCUMENTS

| | | | |
|---|---|---|---|
| 2004/0068196 A1* | 4/2004 | Massicotte ............. | G16H 50/50 600/509 |
| 2009/0156908 A1* | 6/2009 | Belalcazar ............. | A61B 5/287 600/301 |
| 2016/0286297 A1* | 9/2016 | Wang ................... | H04R 1/1016 |

* cited by examiner

*Primary Examiner* — Alyssa M Alter
(74) *Attorney, Agent, or Firm* — United One Law Group LLC; Kongsik Kim; Jhongwoo Peck

(57) ABSTRACT

Earphones comprise a first earphone for collecting a first biosignal and a second earphone for collecting a second biosignal. The second earphone is wirelessly connected to the first earphone and configured to quantize the second biosignal into a second digital signal and transmit the second digital signal to the first earphone together with a set of marker bits representing a time at which the second biosignal is collected. The first earphone includes a biosignal processor configured to quantize the first biosignal into a first digital signal and synchronize the first and second digital signals with reference to the set of marker bits to generate an electrocardiogram (ECG) signal; and a transmitter configured to transmit the ECG signal to a digital device wirelessly connected to the first earphone.

12 Claims, 10 Drawing Sheets

Related U.S. Application Data continuation of application No. PCT/KR2016/005375, filed on May 20, 2016.

(51) Int. Cl.
    *A61B 5/01*     (2006.01)
    *A61B 5/024*     (2006.01)
    *A61B 5/0245*     (2006.01)

BIO-SIGNAL MEASUREMENT MEANS AND BIO-SIGNAL MONITORING SYSTEM

CROSS REFERENCE TO RELATED APPLICATIONS

This application is a Continuation-in-part of U.S. application Ser. No. 15/393,727 filed on Dec. 29, 2016, which is a Continuation of International Application No. PCT/KR2016/005375 filed on May 20, 2016, which claims priority to Korean Application No. 10-2015-0070249 filed on May 20, 2015. The foregoing applications are expressly incorporated herein by reference in their entireties.

TECHNICAL FIELD

The present invention relates to biosignal measurement means and a biosignal monitoring system including, for example, earphones.

RELATED ART

Due to recent rapid progress in science and technology, the quality of life of all mankind is being enhanced and medical environment has changed a great deal. When a medical image is taken by means of X-ray, CT, fMRI or the like, it can take several hours or days to be able to interpret the image.

However, a picture archive communication system (PACS) has been introduced that can enable a medical image to be taken and then transmitted to a monitor screen of a radiology specialist for prompt interpretation thereof. Further, medical equipment for ubiquitous healthcare are widely spread so that self-checks on blood glucose and blood pressure are feasible at anytime and anywhere out of hospital, and diabetic or hypertensive patients are using the equipment at their home or office.

For example, in connection with hypertension, which is one of the principal causes of various diseases and whose prevalence rate is increasing, there is a need for a system for consistent measurement and real-time notification of blood pressure, and various approaches are being attempted.

As one exemplary technique for measuring blood pressure, ubiquitous healthcare (u-Health) has been introduced in which blood pressure can be measured in real time by a blood pressure measurement sensor inserted in a pulmonary artery of a patient suffering a chronic heart disease, and then wirelessly transmitted to an attending doctor so that the doctor can monitor variations in the blood pressure in the pulmonary artery of the patient and give a prescription to the patient. This technique is advantageous in that it can allow a patient to decrease significantly the number of visits to a hospital. While this approach has the advantage of measuring blood pressure continuously and accurately, it accompanies an invasive blood pressure measurement method, and thus can cause operational difficulties and risks of arterial damage, infection, and similar issues.

Therefore, systems for non-invasively measuring blood pressure in real time without inserting any blood pressure measurement sensor in arterial blood vessels are desirable. Further, monitoring blood pressure in a ubiquitous environment and then providing biofeedback on the measured blood pressure to a user so that the user may adjust the blood pressure is also desirable.

Other approaches have been explored. For example, a technique has been introduced in which a cuff is attached to an arm of a user to measure blood pressure. However, according to the technique, someone (the user or another person) must operate a blood pressure measurement apparatus in order to obtain the measured level of the blood pressure, and thus it is difficult to continuously measure the blood pressure.

In order to give warning of hypertension and allow a patient to receive emergency medical treatment in a short time, it is desirable for a technique to continuously measure blood pressure and notify a result of the blood pressure measurement in real time so that the patient may personally prevent and manage the hypertension.

Provided herein is a system in which a wearable device is provided with a non-invasive sensor or sensor module for measuring ECG, PPG and $SpO_2$ signals, and blood pressure is monitored in real time by processing the signals and estimating blood pressure levels. The specific configuration for estimating blood pressure based on measured biosignals is described in the disclosures of Korean Patent Application Nos. 2013-116158 and 2013-116165, which are incorporated herein by reference in their entirety.

In the following, ECG, PPG and $SpO_2$ signals belonging to multiple biosignals mentioned herein will be discussed in more detail. Other biosignals may be further included in the multiple biosignals.

Techniques for measuring an ECG signal, among other biosignals, using earphones have existed in the art. For example, Korean Laid-Open Patent Publication No. 10-2010-0001360 (titled "Portable device for measuring biological signal") discloses a technique for collecting an ECG signal from a first electrode attached to one of earphones and a second electrode attached to an upper arm of a user.

However, such techniques have disadvantages in that biosignals cannot be collected simply by wearing earphones. A separate device must be attached to another body part (e.g., an upper arm of a wearer of the earphones) in order to measure the biosignals.

SUMMARY

As applied below, an electrocardiogram (ECG) is a waveform consisting of a vector sum of action potentials generated by a special excitatory and conductive system of a heart. That is, it is obtained by measuring, from an electrode contacting the outside of a body, a signal related to a vector sum of active potentials generated by the components of the heart such as sinoatrial node (SA node), atrioventricular node (AV node), His bundle, His bundle branch, and Purkinje fibers. For example, the ECG signal can be obtained using a standard limb lead method.

A photoplethysmogram (PPG) signal is a pulse wave signal measured at peripheral blood vessels when blood ejected during a ventricular systole is delivered to the peripheral blood vessels. The PPG signal can be measured using optical properties of biological tissues. For example, it can be obtained by attaching a PPG sensor or sensor module (a light sensor or sensor module) configured to measure a pulse wave signal to a region where peripheral blood vessels are distributed (e.g., fingertips or tiptoes) and then converting variations in blood stream flow (corresponding to variations in the volume of the peripheral blood vessels) into variations in light intensity. The PPG signal can be measured by irradiating red light generated by a light emitter or emitting unit of the PPG sensor or sensor module onto a body part, and then observing variations in the intensity of light reflected from the body part and received by a light receiver or receiving unit. Meanwhile, rather than using only the PPG signal, a correlation between the PPG and ECG signals can be analyzed to derive information such as a pulse transit time (PTT) or a pulse wave velocity (PWV) for use in, for example, diagnosing cardiovascular diseases.

Provided herein, feature points can be obtained from a second derivative of a PPG signal, and time intervals are measured with respect to peak points (or R waves) of an ECG signal to derive PTT and PWV signals for use in diagnosing blood vessel conditions, artery hardening, peripheral circulatory disturbance, and the like.

An oxygen saturation level (or saturation of peripheral oxygen; $SpO_2$) signal is a biosignal representing the content of oxygen present in hemoglobin among various components of blood. The $SpO_2$ signal may be measured by emitting red light and infrared light in alternating periods so that the emitted light is irradiated to peripheral blood vessels of a body part, and then observing variations in the intensity of light reflected from the body part and received by a light receiver or receiving unit. For example, the $SpO_2$ signal can be measured using the above-described PPG sensor or sensor module (which is a light sensor or sensor module).

Earphones using various biosignal measurement methods are provided for use herein.

Provided herein are earphones including biosignal measurement means so that a user can easily measure biosignals of the user in a situation in which the earphones are in use.

Also provided herein are earphones configured to measure biosignals only with sensors attached thereon, thereby avoiding the inconvenience of attaching sensors other than those attached on the earphones to another body part.

Also provided herein are earphones configured to easily synchronize biosignals acquired by the earphones using marker bits associated with times at which the biosignals are acquired.

Also provided herein is a biosignal monitoring system configured to store data obtained by measuring biosignals of a wearer of earphones in real time, and processing the data to provide a variety of presentations.

Also provided herein is a biosignal monitoring system including a communicator or communication module through which a result of real-time monitoring of biosignals of a wearer of earphones can be transmitted to an external server, thereby ensuring an agile and accurate response to an emergency situation in which a problem arises in health condition of the wearer.

The objects of the invention are not limited to the aforementioned ones, and other objects not mentioned herein will be apparently appreciated by those skilled in the art to which the present invention pertains in view of the following detailed description.

Earphones provided herein comprise: a first earphone having a first sensor disposed around an audio output of the first earphone, the first sensor having a first biosignal electrode for collecting a first biosignal; and a second earphone having a second sensor disposed around an audio output of the second earphone, the second sensor having a second biosignal electrode for collecting a second biosignal, wherein the second earphone is wirelessly connected to the first earphone and configured to quantize the second biosignal into a second digital signal and transmit the second digital signal to the first earphone together with a set of marker bits representing a time at which the second biosignal is collected, and wherein the first earphone includes: a biosignal processor configured to quantize the first biosignal into a first digital signal and synchronize the first and second digital signals with reference to the marker bits to generate an electrocardiogram (ECG) signal; and a transmitter configured to transmit the ECG signal to a digital device wirelessly connected to the first earphone.

A biosignal monitoring system provided herein comprises: earphones including a first earphone having a first sensor disposed around an audio output of the first earphone, the first sensor having a first biosignal electrode for collecting a first biosignal, and a second earphone having a second sensor disposed around an audio output of the second earphone, the second sensor having a second biosignal electrode for collecting a second biosignal; and a digital device wirelessly connected to the first earphone, wherein the first earphone includes: a biosignal processor configured to quantize the first biosignal into a first digital signal and synchronize the first and second digital signals with reference to the marker bits to generate an electrocardiogram (ECG) signal; and a transmitter configured to transmit the ECG signal to the digital device, and wherein the digital device is configured to store and manage information on the ECG signal transmitted from the first earphone.

In addition, other configurations can be further provided according to the technical ideas of the invention.

Provided herein are earphones including biosignal measurement means so that a user can easily measure biosignals of the user in a situation in which the earphones are in use.

Also provided herein are earphones configured to measure biosignals only with sensors attached thereon, thereby avoiding the inconvenience of attaching sensors other than those attached on the earphones to another body part.

Also provided herein are earphones configured to easily synchronize biosignals acquired by the earphones using marker bits associated with times at which the biosignals are acquired, thereby resolving time errors.

Data obtained by measuring biosignals of a wearer of earphones in real time can be stored and processed to provide a variety of presentations so that variations in the biosignals of the user over time can be easily recognized, thereby providing feedback on the variations in the biosignals over time while the user is carrying out an exercise or a diet for a specific period of time.

Also provided herein is a biosignal monitoring system with earphones, a digital device to which the earphones are connected, and a communicator or communication module through which a result of real-time monitoring of biosignals of a wearer of the earphones can be transmitted to an external server, thereby ensuring an agile and accurate response to an emergency situation in which a problem arises in health condition of the wearer.

DETAILED DESCRIPTION

Figure 1:
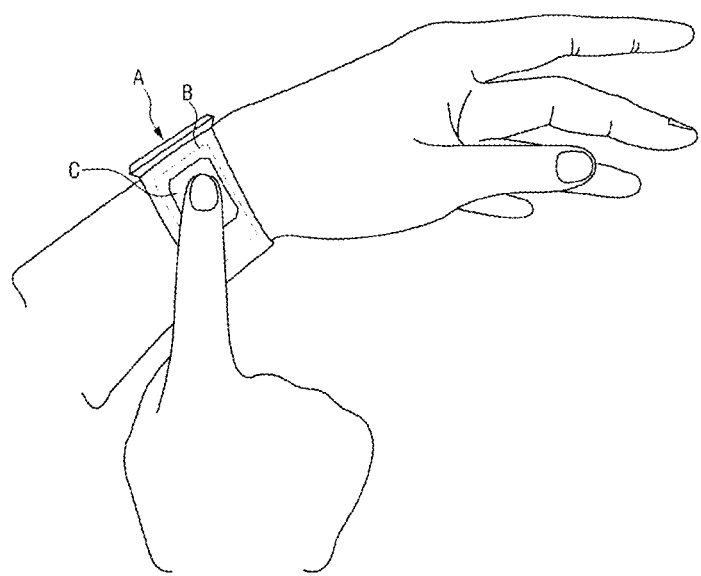
FIG. 1 shows one embodiment of a blood pressure measurement method.

Hereinafter, preferred embodiments of the present invention will be described in detail with reference to the accompanying drawings to enable those skilled in the art to easily implement the invention.

In order to clearly illustrate the present invention, detailed descriptions on the elements irrelevant to the invention will be omitted, and the same elements will be denoted by the same reference numerals throughout the entire specification. Further, the shape and size of each element shown in the drawings are arbitrarily shown for convenience of illustration, and the present invention is not necessarily limited to the shown shape and size. That is, specific shapes, structures and characteristics described herein may be implemented as modified from one embodiment to another without departing from the spirit and scope of the invention. Furthermore, it shall be understood that the locations or arrangements of individual elements may also be modified without departing from the spirit and scope of the invention. Therefore, the following detailed description is not to be taken in a limiting sense, and the scope of the invention is to be taken as encompassing the scope of the appended claims and all equivalents thereof.

Although preferred embodiments of the present invention have been described with reference to the accompanying drawings, it will be appreciated by those skilled in the art to which the present invention pertains that the invention may be implemented in other specific forms without changing the technical ideas or essential features thereof. Therefore, it should be understood that the above-described embodiments are not restrictive but illustrative in all aspects.

FIG. 1 shows one embodiment of a blood pressure measurement method. The main body of a blood pressure measurement apparatus shown in FIG. 1 includes a display A, a first electrode B, and a second electrode C. The first electrode B for biosignal measurement can be provided on the back side of the main body (i.e., the inner side contacting a wrist when the device is worn thereon). The second electrode C for biosignal measurement can be provided on the front side of the main body (i.e., the outer side not contacting the wrist when the device is worn thereon). When a user wears the main body on his/her wrist and puts a body part such as a finger into contact with the second electrode C while the first electrode B contacts the wrist of the user, an ECG signal of the user's body can be measured through the first electrode B and the second electrode C. Further, by using a separate measurement electrode not shown in FIG. 1, the device can be connected to a measurement module configured to measure PPG and SpO$_2$ signals. The measured level of the blood pressure can be calculated based on the biosignals measured as above, and displayed on the display A so that the user can recognize it.

Figure 2:
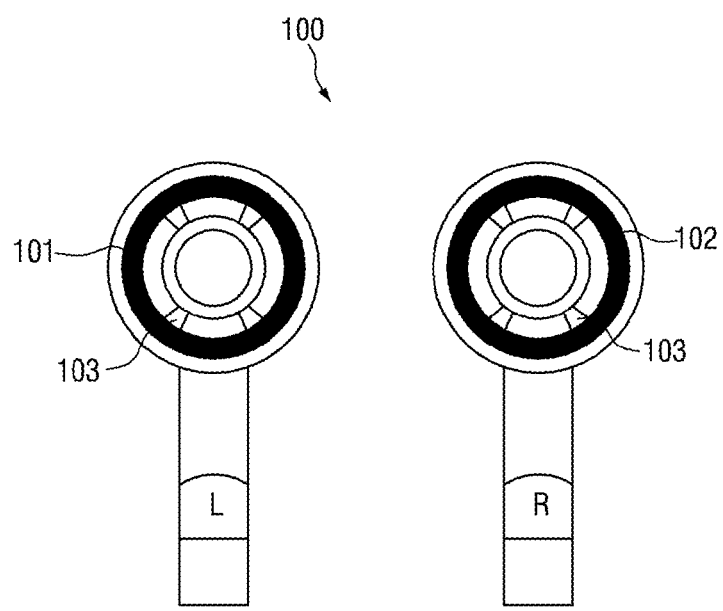
FIG. 2 shows a first electrode and a second electrode for ECG measurement around audio outputs of both earphones.

FIG. 2 shows a first electrode 101 and a second electrode 102 for ECG measurement that can be provided around audio outputs or output units of both earphones 100.

Both of the left and right earphones are shown in FIG. 2. Each of the left and right earphones can include an audio output or output unit 103. The first electrode 101 and the second electrode 102 can be provided around the audio outputs 103 of the earphones 100. The first electrode 101 can be provided at the left earphone, and the second electrode 102 can be provided at the right earphone. When providing the first electrode 101 and the second electrode 102, it is preferable that, while the earphones 100 are worn on a user's ears, both of the first and second electrodes 101 and 102 can be in contact with inner skin of the ears. In other embodiments, if the first electrode 101 and the second electrode 102 are provided around the audio outputs 103, they can also be provided in a variety of other ways (e.g., provided at the sides of eartips covering the audio outputs 103) without being limited to the illustration of FIG. 2.

An electric signal input can be received from electrodes contacting at least two different body parts of a user, in order to measure an ECG signal. When the user wears a device in the form of a watch on his/her wrist, a first electrode can be provided on the inner side of the device contacting the wrist, and a second electrode can be provided on the outer side of the device not contacting the wrist so that the user can put a body part such as a finger into contact with the second electrode to measure the ECG signal.

Similar to the embodiment in FIG. 1, the at least two different body parts of the user in the present embodiment correspond to inner skin of the left ear and of the right ear.

Figure 3:
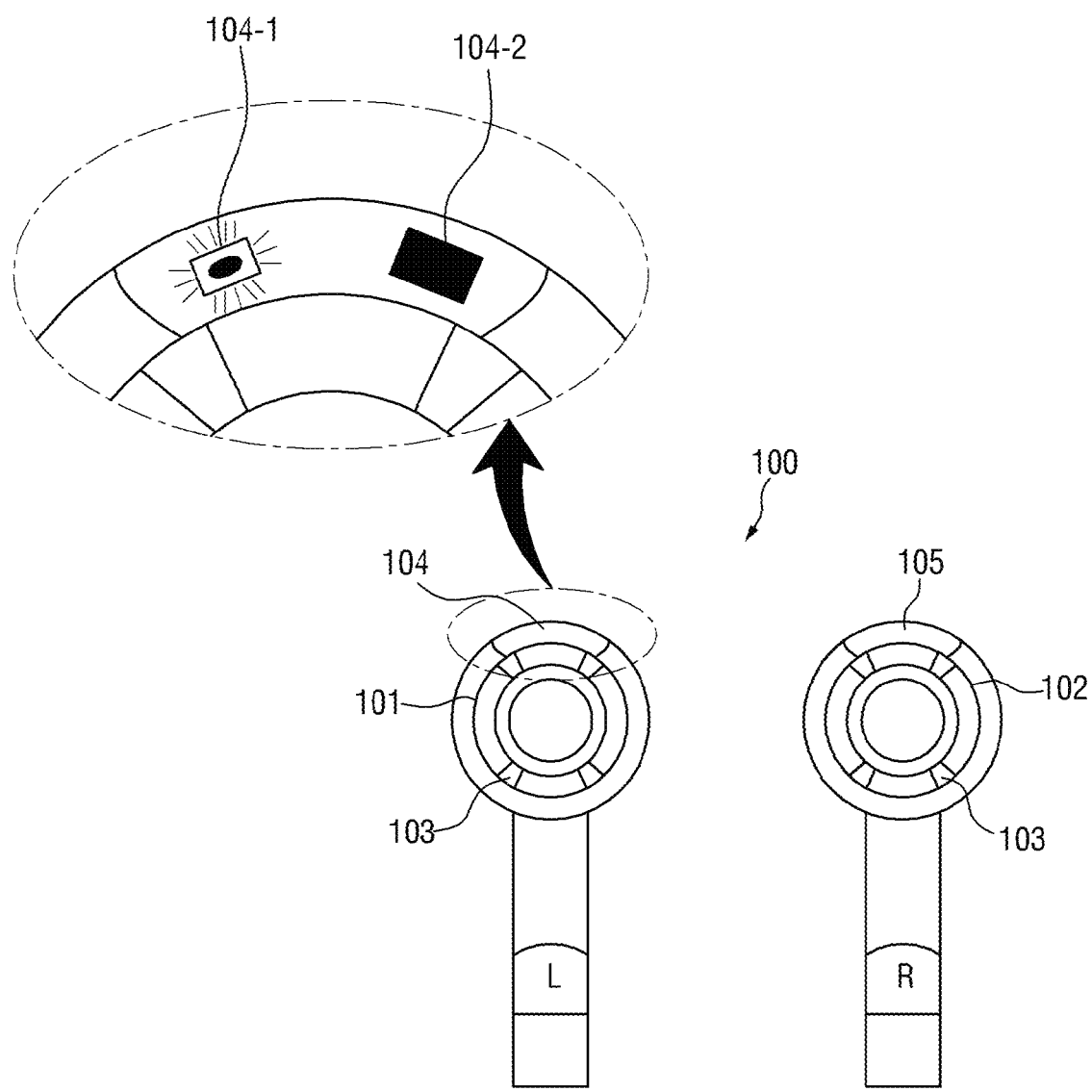
FIG. 3 shows sensors for collecting other biosignal information provided around the audio outputs of the earphones.

FIG. 3 shows that, in addition to the electrodes 101, 102 for ECG measurement, sensors for collecting other biosignal information can be provided around the audio outputs 103 of the earphones 100.

Both of the earphones are provided with the first electrode 101 and the second electrode 102 for ECG measurement, respectively. In the embodiment shown in FIG. 3 however, sensors for collecting biosignals that can be measured by non-electrode type sensors can be additionally disposed at body parts other than those at which the first electrode 101 and second electrode 102 are disposed.

The sensors for collecting the biosignals can include a sensor or sensor module 104 for measuring, for example, PPG and SpO$_2$ signals.

The sensor or sensor module can be configured to PPG and SpO$_2$ signals and irradiates red light onto an ear of a user of the earphones using a red light source, and measures light transmitted or reflected therefrom using a light sensor, thereby measuring blood stream flow in peripheral blood vessels therein.

If the earphones are formed to fit into earholes as shown in FIGS. 2 and 3, a reflective measurement module can be employed. In this case, the measurement module for PPG and SpO$_2$ signals is a reflective measurement module. The reflective measurement module can include a light emitter or emitting unit 104-1 with a red LED for generating light having a wavelength of about 660 nm and an infrared LED for generating light having a wavelength of about 940 nm, and a light receiver or receiving unit 104-2 with an optic module to which a photo diode and a photo transistor are attached.

Figure 4:
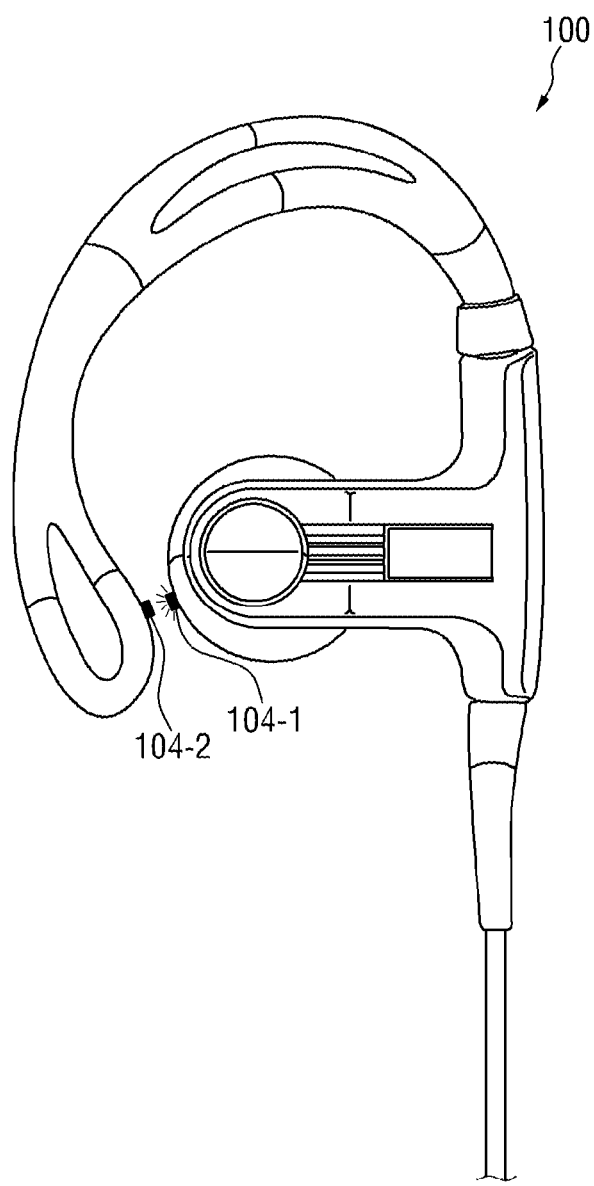
FIG. 4 shows an embodiment in which modules for measuring PPG and $SpO_2$ signals are configured as transmissive modules when earphones are sports-type earphones having structures for covering the periphery of ears.

Meanwhile, other types of earphones having audio outputs or output units fitted into earholes and covering the exterior of ears (e.g., earphones having separate structures for covering the periphery of ears to prevent the earphones from falling off from the ears even during strenuous exercise of a wearer of the earphones (see FIG. 4)) can include a transmissive measurement module with a light emitter or emitting unit 104-1 disposed around the audio output 103, and a light receiver or receiving unit 104-2 disposed at the part that covers the periphery of an ear and faces the light emitter with the skin of the ear being interposed therebetween while the earphones are worn. In this case, the measurement module for PPG and $SpO_2$ signals can be a transmissive measurement module. The transmissive measurement module can include ca light emitter or emitting unit with a red LED for generating light having a wavelength of about 660 nm and an infrared LED for generating light having a wavelength of about 940 nm, and a light receiver or receiving unit with an optic module to which a photo diode and a photo transistor are attached.

The above-described sensor or sensor module 104 for measurement of PPG and $SpO_2$ signals is not necessarily provided at each of the left and right earphones, because no signals from at least two different body parts are necessary to obtain desired biosignals.

In addition to the sensor 104 for measuring PPG and $SpO_2$ signals, sensors or sensor modules for measuring other biosignals can also be disposed in and/or around the system. For example, the sensor 104 configured to measure PPG and $SpO_2$ signals can be disposed at the left earphone, and a body temperature module 105 configured to measure body temperature can be disposed at the right earphone. However, without being limited to the above, modules for measuring various biosignals (e.g., a module for measuring pulse) can be further disposed around the audio outputs 103.

As described above, when the earphones 100 include all of the modules for measuring ECG, PPG and $SpO_2$ signals around the audio output 103, blood pressure levels of a user can be advantageously estimated. In this connection, a method of estimating or calculating blood pressure levels of a user using the above three biosignals has been described herein. Such a method is described in detail in the disclosures of Korean Patent Application Nos. 2013-116158 and 2013-116165 of the inventor, which are incorporated herein by reference in their entirety.

Excessively high or low blood pressure levels can cause an emergency situation that can permanently and critically damage the body. The ability to monitor blood pressure levels in real time while earphones are worn can have a very beneficial effect in coping with the emergency situation while ensuring that the user will comply in wearing the measurement device (e.g. the earphones). Coping with the emergency situation will be described in detail in connection with another embodiment in which the earphones and the digital device connected thereto are configured as a single system.

The configurations of the sensor or sensor units of the earphones for acquiring a variety of biosignal information have been described so far. The configuration of sensors provided herein does not require separate sensors or sensor units (e.g., those separately worn on other body parts such as arms or legs of the user) other than those disposed around the audio outputs 103 of the earphones 100. In contrast, previous arrangements, such as the technique of Korean Laid-Open Patent Publication No. 10-2010-0001360 (titled "Portable device for measuring biological signal"), require attaching a first electrode to one of the earphones and a second electrode to an upper arm of the user to collect ECG signals. This technique is inconvenient because biosignals cannot be collected only by wearing the earphones. A separate device must be attached to another body part in order to measure biosignals, creating additional steps to use the device and additional chances of faulty placement or noncompliance by the user. The arrangement provided herein, however, allows biosignal information to be acquired only by biosignal measurement sensors attached to the earphones, and the difference allows for easier use. For example, in the course of enjoying music as usual, biosignals can be measured without any inconvenient actions such as attaching a separate biosignal measurement sensor to the body of a user.

Figure 5:
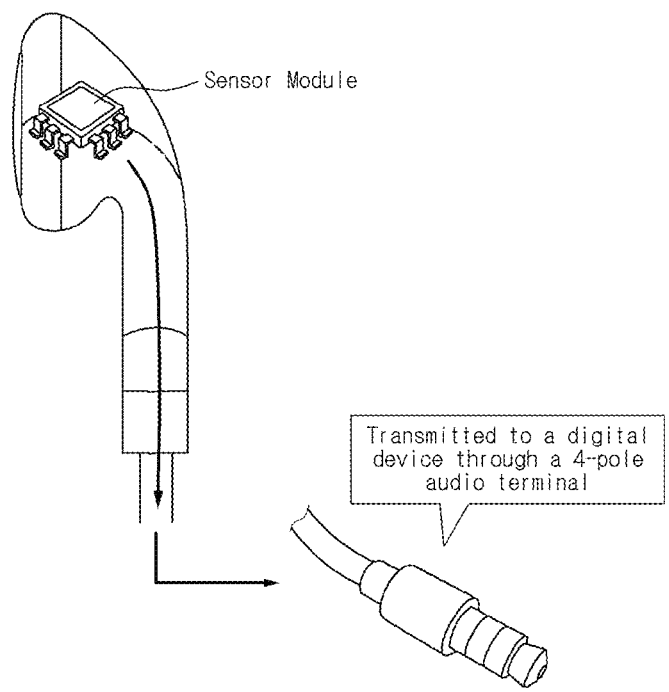
FIG. 5 shows that biosignal information acquired by the biosignal sensors disposed around the audio outputs of the earphones is transmitted through an earphone cable.

FIG. 5 shows that biosignal information acquired by the biosignal sensors disposed around the audio outputs 103 of the earphones 100 is transmitted through an earphone cable. Biosignal information is collected from various sensors or sensor modules disposed around the audio outputs 103 of the earphones 100. A variety of biosignal information collected from the sensors can be provided to a digital device to which the earphones are connected, through the earphone cable and a 4-pole terminal.

The earphones can be connected to the digital device through the cable, and the earphones can be wirelessly connected to the digital device. When the earphones are wireless earphones, they can be connected to the digital device using Bluetooth, WiFi, or other short-range communication technologies. In some embodiments, the earphones can include a short-range communicator or communication module configured to transmit biosignal information to the digital device, and biosignal information acquired by the sensors or sensor modules is transmitted to the communicator so that the biosignal information is transmitted to the digital device through the communicator. For example, when the earphones are connected to the digital device using Bluetooth Low Energy (BLE) communication, the earphones may be specified as a central earphone serving as a master and a peripheral earphone serving as a slave, respectively, and the biosignal information may be transmitted from the central earphone to the digital device.

Figure 6:
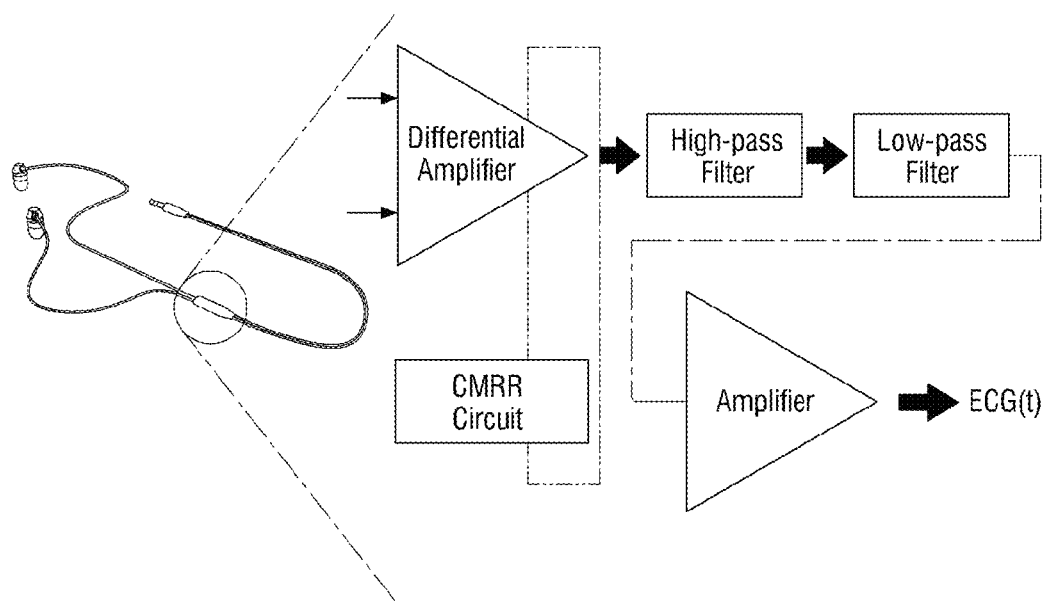
FIG. 6 shows a biosignal processing unit provided to the earphones.

FIG. 6 shows a biosignal processor or processing unit that can be provided to the earphones.

Biosignals are not only weak in intensity, but also tend to mix with other noises. This means that it is inevitably necessary to have a configuration for processing collected biosignals into signals suitable for use. For example, a biosignal processor or processing unit for performing such a function can include signal amplifiers, filters, analog-digital converters and the like, and the block diagram in the right side of FIG. 6 shows the signal amplifiers and filters excluding the analog-digital converters. As shown in the left side of FIG. 6, the signal amplifiers and filters can be located where the output cables of the left and right earphones meet. As for wireless earphones in which the earphones are not separated from but integrally formed with a receiver (which receives an audio output signal from a digital device to which the earphones are connected), the output cables of the left and right earphones can be connected to the receiver without directly meeting each other. In the case of such wireless earphones, the signal amplifiers and filters can be combined with the receiver.

Meanwhile, the scope of the invention is not limited to embodiments in which the signal amplifiers and filters are provided where the output cables of the left and right earphones meet or at the receiver of the wireless earphones, as shown in the left side of FIG. 6. The signal amplifiers and filters may not be provided at a part of the earphones, but can be provided in the digital device to which the earphones are connected. That is, the signals from the sensors or sensor units located around the audio outputs 103 of the earphones may not be amplified and filtered in the course of being transmitted to the digital device, but can be amplified and filtered through the signal amplifiers and filters provided in the digital device, and then analog-digital converted.

In the earphones according to one embodiment, whether the signal amplifiers and filters are provided in the earphone device, or signal amplification and filtering are not performed in the earphone device but in the digital device to which the earphones are connected, a first biosignal can be obtained from the first electrode 101 formed around the audio output 103 of one of the earphones, and a second biosignal can be obtained from the second electrode 102 formed around the audio output 103 of the other of the earphones. By amplification and filtering, more specifically band-pass filtering of the first and second biosignals obtained as above, desired biological information (e.g., electrocardiogram signals (ECG(t)) can be generated.

The earphones according to one embodiment can include their own storage unit. In this case, biosignals collected from various sensors including the first electrode 101 and the second electrode 102 are stored in the storage unit. When the collected biosignals are stored, the times and/or conditions in which the biosignals are collected can also be stored together in the storage unit. Here, the conditions in which the biosignals are collected can be, for example, atmospheric conditions (such as temperature and pressure) or geographical conditions (such as latitude, longitude, and altitude) at the time of collecting the biosignals, and can also include ambient noises, images and the like. The storage of the conditions in which the biosignals are collected can be selectively performed according to additional sensors and input devices connected to the earphones. The conditions in which the biosignals are collected are not limited to those listed above.

Meanwhile, the earphones according to one embodiment can further include their own display or display unit. In this case, the display or display unit can display information on the biosignals stored in the storage unit according to a selection of a wearer of the earphones, or in a predetermined manner.

Further, the earphones according to one embodiment can also have their own battery. In general, earphones do not have a music playback function, and can play music only when they are connected to a digital device such as an MP3 player or a smartphone. Thus, conventional earphones could not be independently utilized. However, unlike the conventional earphones, the earphones provided herein can include various sensors and/or sensor devices that are capable of collecting biosignals and disposed around the audio outputs 103, and means for storing and displaying biosignal information collected therefrom, and thus can function independently of the connected digital device. The earphones can include their own battery for the independent utilization thereof. In the embodiments in which the earphones are independently utilized, it is preferable that the biosignal processing unit including the above-described signal amplifiers, filters and/or analog-digital converters is provided in the earphones, so that the biosignals collected from the various sensors can be processed into a form suitable for storage, digital display and the like, before they are stored in the storage unit included in the earphones and displayed on the display. The signal processing method will be discussed in more detail below with reference to FIG. 7.

The self-contained battery provided in the earphones can be implemented in the form of a rechargeable secondary battery, and the method of charging the battery can be implemented by a variety of different techniques, for example a variety of wired and wireless means known by one skilled in the art at the time of filing. More specifically, in the case of wireless charging, the battery can be wirelessly charged from a power source of a digital device when it is wirelessly connected to the digital device, or can be charged through a wireless charging device separate from the digital device. In the case of wired charging, the battery can be charged using wires from a power source of a digital device when it is connected by wires to the digital device, or may be charged by wires through various cable connections such as a USB cable connection to a separate power source.

Figure 7:
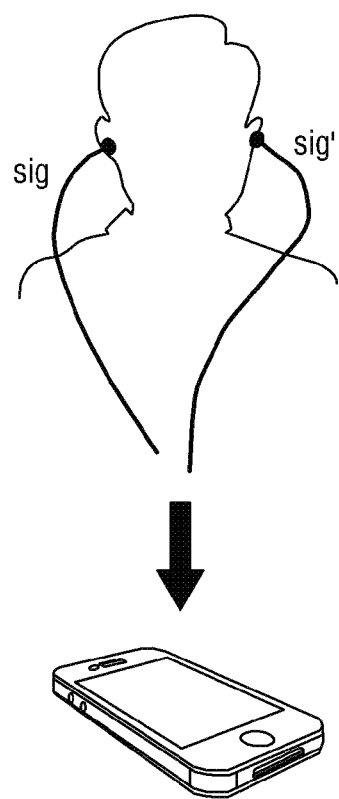
FIG. 7 shows electrocardiogram signal information respectively collected from the left and right earphones according to the invention being alternatively transmitted.
Figure 7:
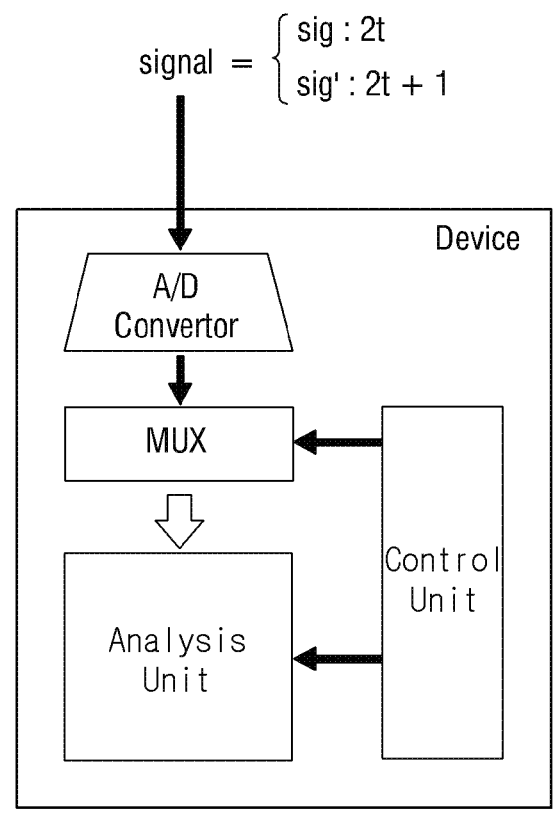

FIG. 7 shows that electrocardiogram signal information respectively collected from the left and right earphones can be alternately transmitted.

In order to process ECG signals, signals measured simultaneously in the left and right earphones can be required. For transmission of the simultaneously measured biosignals, a time-division multiplexing (TDM) technique can be employed in one embodiment.

More specifically, referring to FIG. 7, the earphones according to one embodiment can define a plurality of first time slots ($2t$ in FIG. 7) and a plurality of second time slots ($2t+1$ in FIG. 7), which are alternately arranged in a time dimension using a time division technique, so that a first biosignal (Sig in FIG. 7) obtained from the first electrode 101 of the earphone worn on the user's right ear can be received only in the first time slot ($2t$), and a second biosignal (Sig' in FIG. 7) obtained from the second electrode 102 of the earphone worn on the user's left ear can be received only in the second time slot ($2t+1$).

Referring further to FIG. 7, both of the first biosignal (Sig) received via the first time slot ($2t$) and the second biosignal (Sig') received via the second time slot ($2t+1$) can be converted into digital signals by performing analog-digital (A/D) conversion on the first biosignal (Sig) and the second biosignal (Sig'). By multiplexing (or taking multiple signals and combining them into one signal over a shared medium) of the first and second biosignals converted as above (MUX in FIG. 7), the final biosignals can be generated.

According to one embodiment, the signals can be processed by a microcontroller unit (MCU) having an ADC resolution of 8-bit size and 1,024 Hz speed, and the left and right earphones can transmit 8-bit signals, respectively. In this case, the MCU can process the biosignal transmitted from the right earphone at 512 Hz at the time of $2t$, and process the biosignal transmitted from the left earphone at 512 Hz at the time of $2t+1$, so that continuous processing can be implemented.

Meanwhile, the scope of the invention is not limited to the embodiments in which the biosignals are transmitted through the above-described time division technique. Embodiments are also encompassed in which a variety of biosignal information obtained by the sensor units of the left and right earphones can be simultaneously transmitted to and processed by the digital device, without applying the time division technique.

Figure 8:
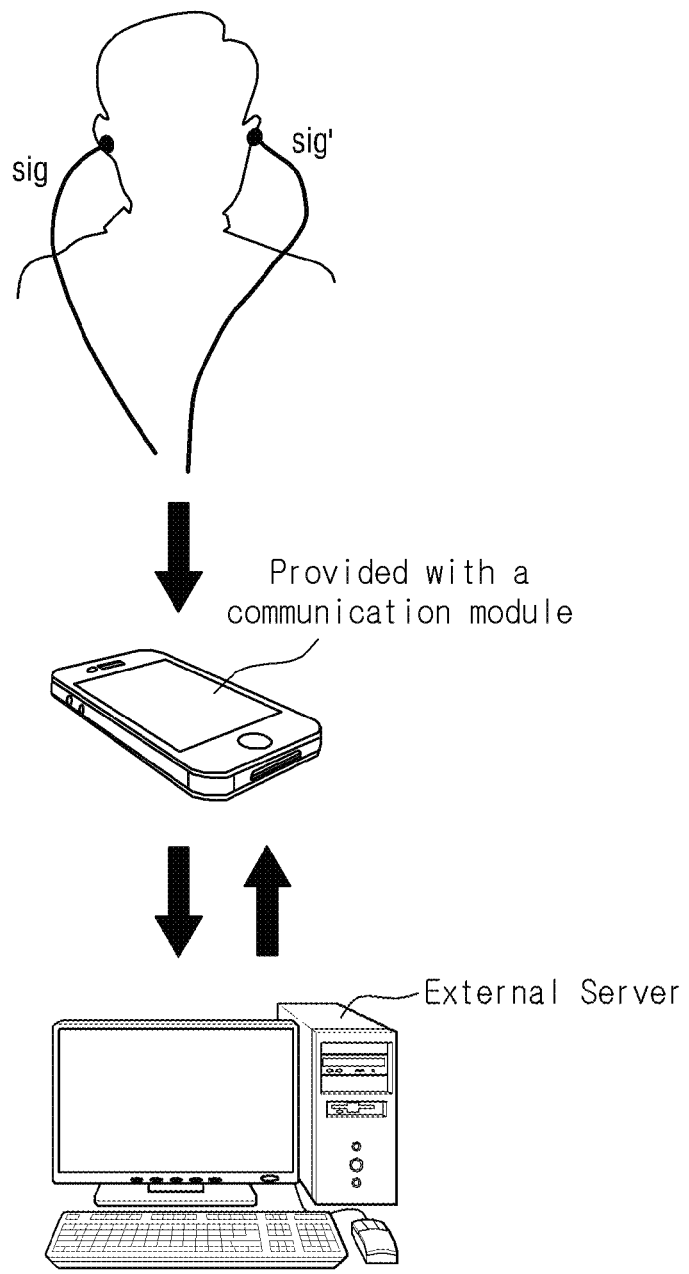
FIG. 8 is a conceptual diagram showing that a system with the earphones and the digital device connected thereto transmits acquired biosignal information to an external server through a communication module thereof.

FIG. 8 is a conceptual diagram showing a system including the earphones discussed herein and the digital device connected thereto can transmit acquired biosignal information to an external server through a communication module thereof.

A method of calculating blood pressure levels based on measured ECG, PPG and $SpO_2$ biosignals is provided herein, and this unique method is disclosed in Korean Patent Application Nos. 2013-116158, 2013-116165, and the like, incorporated herein by reference. When the method of calculating blood pressure levels is performed by a system with earphones and a digital device being connected thereto and including a calculator or calculation means, the system can calculate blood pressure levels of a wearer of the earphones in real time and notify the wearer of the levels via a screen of the digital device. Further, the system can store and manage the blood pressure levels using a storage means included in the system, and can display variations in the blood pressure levels over time.

Meanwhile, the system can also include a communicator or communication module. In this case, a system in which variations in a variety of biosignal information (e.g., ECG, PPG, $SpO_2$, body temperature, pulse, blood pressure, etc.) are stored and managed can further perform a server function.

When the above system is configured to perform the server function, the system can autonomously recognize a health risk of the wearer of the earphones based on the obtained biosignal information, or the obtained biosignal information can be transmitted to an external server through the communicator or communication module so that the external server can recognize the health risk of the wearer of the earphones.

In some embodiments, the system can be configured to autonomously recognize a health risk of the wearer of the earphones. In such an embodiment, the digital device of the system can include a storage means and a calculator or calculation means. In this case, the system can be configured to autonomously determine whether the biosignal information acquired by the earphones falls within a predetermined range for alarm generation. If it is determined that specific biosignal information such as blood pressure information indicates excessive hypertension or excessive hypotension beyond a predetermined range, the system can notify the health risk of the wearer to an external server of a hospital, an emergency rescue agency, the wearer, or the like through the communicator. In this case, if the digital device is provided with a GPS module capable of receiving GPS data, the GPS data can be transmitted together to cope with the emergency situation more effectively.

The system can also be configured to transmit the obtained biosignal information to an external server through the communication module, so that the external server can recognize a health risk of the wearer of the earphones. The determination of the health risk can be directly made from any one or more types of biosignal information in various embodiments, but may also require a multilateral examination of variations in a variety of biosignal information in other embodiments. In some embodiments in order to precisely analyze the health condition, the multilateral examination of the variations can be performed by an institution where vast amounts of data can be stored/analyzed and skilled medical personnel reside, rather than being autonomously performed by the digital device. To this end in some embodiments, the system does not autonomously determine whether biosignal information acquired by the earphones falls within a predetermined range for alarm generation, but transmits a variety of acquired biosignal information to an external server such as a hospital server through the communicator or communication module provided in the system. In other embodiments, the system can also be configured to preliminarily determine whether the biosignal information acquired by the earphones falls within a predetermined wider range, and then transmit the biosignal information to an external server through the communicator or communication module provided in the system only when it falls within the predetermined wider range. Such an embodiment is beneficial because, when the system is configured to transmit all the biosignal information collected therein to an external server in real time, the processing load at the external server will be increased and the communication network will run the risk of being overloaded.

The external server that receives the biosignal information of the wearer of the earphones transmitted by the system can cumulatively store variations in a variety of biosignal information in a storage area corresponding to a specific user ID, and then a health risk factor analysis can be performed by a specific program, or real-time biosignal information can be compared with the accumulated data and analyzed by skilled personnel. When the health risk of the wearer of the earphones is recognized by the external server in the above manner, the system can receive a warning signal from the external server through the communicator or communication module, and can handle it in various ways, for example, by visually indicating it on a display provided in the digital device, or by generating an audible warning sound via the earphones. The system that receives the warning signal from the external server can collect the current position information from the GPS module included in the digital device, and transmit it to the external server (e.g., at an hospital or an emergency rescue agency) to cope with the emergency situation more effectively.

Figure 9:
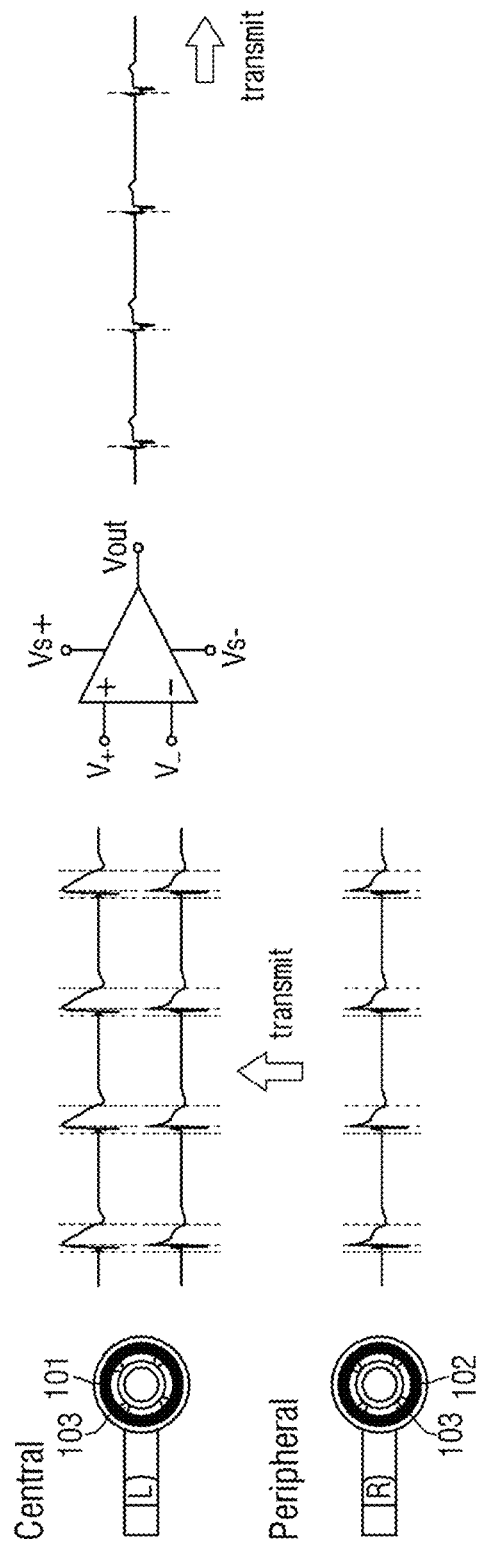
FIGS. 9 and 10 show synchronization of biosignals respectively collected from a left earphone and a right earphone according to the present invention.
Figure 10:
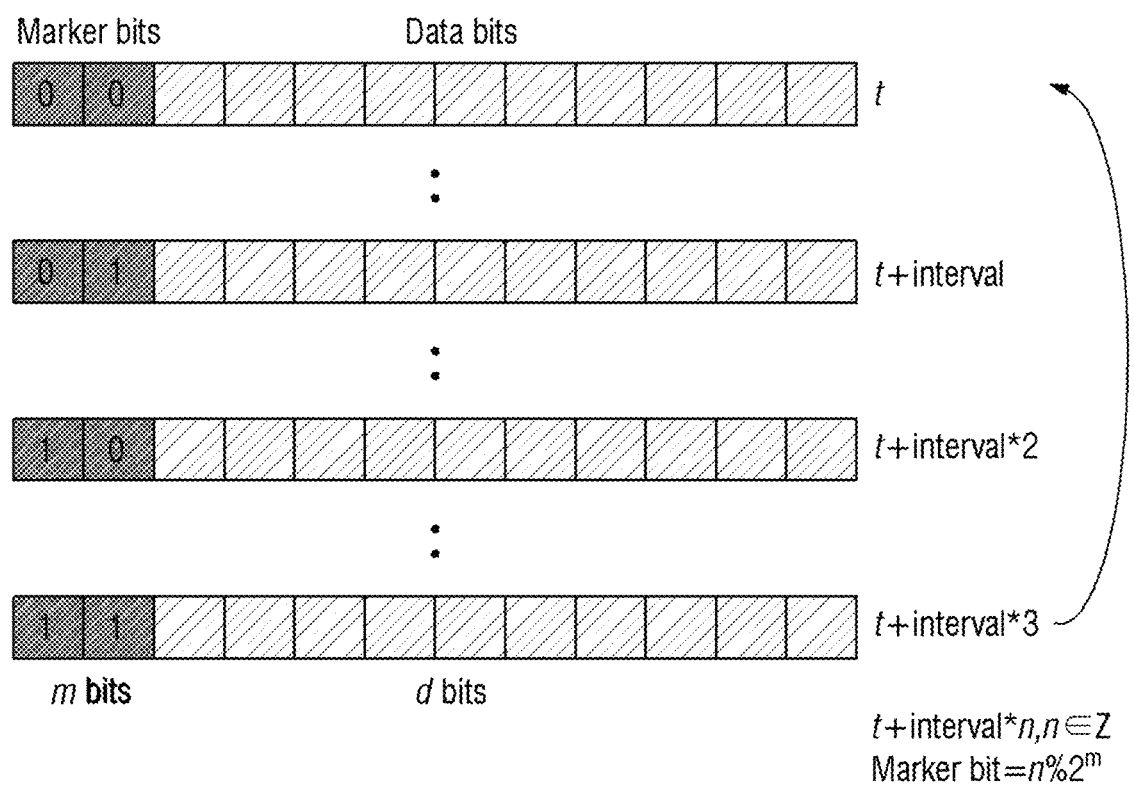

FIGS. 9 and 10 show how to synchronize biosignals respectively collected from a left earphone and a right earphone according to the invention.

In order to generate an ECG signal from the biosignals acquired from the left and right earphones, synchronization between the signals measured by the left and right earphones may be required.

Specifically, according to one embodiment of the invention, a first earphone (or the left earphone) may quantize a first biosignal acquired from a first sensor of the first earphone into a first digital signal, and a second earphone (or the right earphone) may quantize a second biosignal acquired from a second sensor of the second earphone into a second digital signal. Thereafter, the first and second digital signals may be synchronized with each other and then differentially amplified to generate an ECG signal.

For example, referring to FIG. 9, it may be assumed that the earphones are Bluetooth-based wireless earphones, and the first and second earphones serve as a central earphone and a peripheral earphone, respectively. In this case, the second earphone may transmit the second digital signal to the first earphone together with a set of marker bits representing a time at which the second biosignal is acquired. Further, the first earphone may synchronize the first and second digital signals with reference to the transmitted set of marker bits, and perform differential amplification on the synchronized digital signals to generate an ECG signal. Here, the synchronization may be performed such that at least one of times of the first and second digital signals is corrected on the basis of a time error specified from the marker bits, and when signal measurement sampling rates of the first and second digital signals are different, the difference between the sampling rates is also considered in the correction (e.g., through resampling or the like). Meanwhile, the generated ECG signal may be transmitted to a digital device that is wirelessly connected to the first earphone.

Meanwhile, the above marker bits may function similarly to time stamps, and may be transmitted according to a protocol associated with signal transmission and reception between the earphones (e.g., a BLE protocol).

For example, referring to FIG. 10, the second earphone may provide one piece of data consisting of data bits for the second digital signal (shown as "Data bits" in FIG. 10) and marker bits (shown as "Marker bits" in FIG. 10) associated with the time at which the second biosignal corresponding to the second digital signal is acquired, according to a transmission/reception protocol between the first and second earphones. That is, a time error between the first and second digital signals of the first and second earphones may be specified on the basis of the marker bits, so that synchronization between the first and second digital signals may be performed through, for example, offset removal or frequency drift estimation.

More specifically, a value of the marker bits may be determined with reference to a length of the marker bits and a relationship between the time at which the second biosignal is acquired and a predetermined reference time (which may be a time at which the second biosignal is acquired for the first time, or a time specified by the user). For example, when it is assumed that the marker bits are two bits long, a time at which the second biosignal is acquired for the first time is denoted as "t", and a sampling interval for the second biosignal is denoted as "interval", the value of the marker bits for the second digital signal corresponding to the second biosignal acquired for the first time may be determined as 0% $2^2$ (i.e., "00") since the marker bits are two bits long and the difference between the time at which the second biosignal is acquired and the reference time is 0×interval. Next, when the second biosignal is acquired for the second time at t+interval, the value of the marker bits for the second digital signal corresponding to the second biosignal acquired for the second time may be determined as 1% $2^2$ (i.e., "01") since the marker bits are two bits long and the difference between the time at which the second biosignal is acquired and the reference time is 1×interval. Next, when the second biosignal is acquired for the third time at t+interval*2, the value of the marker bits for the second digital signal corresponding to the second biosignal acquired for the third time may be determined as 2% $2^2$ (i.e., "10") since the marker bits are two bits long and the difference between the time at which the second biosignal is acquired and the reference time is 2×interval. Next, when the second biosignal is acquired for the fourth time at t+interval*3, the value of the marker bits for the second digital signal corresponding to the second biosignal acquired for the fourth time may be determined as 3% $2^2$ (i.e., "11") since the marker bits are two bits long and the difference between the time at which the second biosignal is acquired and the reference time is 3×interval.

Meanwhile, the scope of the invention is not necessarily limited to the embodiments in which the marker bits are transmitted according to the above-described transmission/reception protocol, and may encompass embodiments in which the marker bits are transmitted according to a separately defined protocol or in addition to other transmission/reception data. Further, the lengths of the data bits and marker bits and the method of determining the value of the marker bits are not necessarily limited to the above embodiments, and may be diversely changed as long as the objects of the invention may be achieved.

Further, the time synchronization method for generating an ECG signal as described above may also be extensively applied to a wireless ECG measurement device (e.g., a band device attached to a wrist or ankle to measure ECG signals) as well as the earphones.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. Earphones comprising:
a first earphone having a first sensor disposed around an audio output of the first earphone, the first sensor having a first biosignal electrode for collecting a first biosignal; and
a second earphone having a second sensor disposed around an audio output of the second earphone, the second sensor having a second biosignal electrode for collecting a second biosignal,
wherein the second earphone is wirelessly connected to the first earphone and configured to quantize the second biosignal into a second digital signal and transmit the second digital signal to the first earphone together with a set of marker bits representing a time at which the second biosignal is collected,
wherein the first earphone includes:
a biosignal processor configured to quantize the first biosignal into a first digital signal and synchronize the first and second digital signals with reference to the set of marker bits to generate an electrocardiogram (ECG) signal; and
a transmitter configured to transmit the ECG signal to a digital device wirelessly connected to the first earphone, and
wherein values of the set of marker bits are determined based on a bit-length of the set of marker bits and a number of sampling intervals between the time at which the second biosignal is collected and a predetermined reference time.

2. The earphones of claim 1, wherein the biosignal processor is configured to synchronize the first and second digital signals by correcting at least one of times of the first and second digital signals on the basis of a time error specified from the set of marker bits.

3. The earphones of claim 2, wherein the biosignal processor is configured to correct at least one of times of the first and second digital signals on the further basis of sampling rates of the first and second digital signals.

4. The earphones of claim 1, wherein the biosignal processor is configured to perform differential amplification on the synchronized digital signals to generate the ECG signal.

5. The earphones of claim 1, wherein the second earphone is configured to combine data bits corresponding to the second digital signal with the set of marker bits and transmit the combined bits to the first earphone.

6. A biosignal monitoring system, comprising:
earphones including:
a first earphone having a first sensor disposed around an audio output of the first earphone, the first sensor having a first biosignal electrode for collecting a first biosignal, and
a second earphone having a second sensor disposed around an audio output of the second earphone, the second sensor having a second biosignal electrode for collecting a second biosignal; and
a digital device wirelessly connected to the first earphone,
wherein the first earphone includes:
a biosignal processor configured to quantize the first biosignal into a first digital signal and synchronize the first and second digital signals with reference to the set of marker bits to generate an electrocardiogram (ECG) signal; and a transmitter configured to transmit the ECG signal to the digital device, wherein the digital device is configured to store and manage information on the transmitted ECG signal, and wherein values of the set of marker bits are determined based on a bit-length of the set of marker bits and a number of sampling intervals between the time at which the second biosignal is collected and a predetermined reference time.

7. The biosignal monitoring system of claim 6, wherein the biosignal processor is configured to synchronize the first and second digital signals by correcting at least one of times of the first and second digital signals on the basis of a time error specified from the set of marker bits.

8. The biosignal monitoring system of claim 7, wherein the biosignal processor is configured to correct at least one of times of the first and second digital signals on the further basis of sampling rates of the first and second digital signals.

9. The biosignal monitoring system of claim 6, wherein the biosignal processor is configured to perform differential amplification on the synchronized digital signals to generate the ECG signal.

10. The biosignal monitoring system of claim 6, wherein the second earphone is configured to combine data bits corresponding to the second digital signal with the set of marker bits and transmit the combined bits to the first earphone.

11. The biosignal monitoring system of claim 6, wherein the digital device is configured to determine whether the information on the ECG signal falls within a preliminary emergency range and transmit the information on the ECG signal to an external server when it is determined that the information on the ECG signal falls within the preliminary emergency range, and wherein the external server is configured to recognize an emergency situation in view of the transmitted information on the ECG signal and transmit a warning signal to the digital device when the emergency situation is recognized.

12. The biosignal monitoring system of claim 11, wherein the digital device includes a GPS module configured to calculate GPS coordinates thereof, and wherein the digital device is configured to transmit GPS information acquired from the GPS module to the external server when the digital device receives the warning signal.

* * * * *